US007001880B1

(12) United States Patent
Yomogida et al.

(10) Patent No.: US 7,001,880 B1
(45) Date of Patent: Feb. 21, 2006

(54) METHOD OF COLLECTION OF FRAGRANCE INGREDIENT, PERFUME COMPOSITION CONTAINING THIS FRAGRANCE INGREDIENT AND COSMETICS CONTAINING THIS FRAGRANCE INGREDIENT

(75) Inventors: Katsuyuki Yomogida, Kanagawa (JP); Seiichi Hirose, Kanagawa (JP); Masanori Yoshimura, Kanagawa (JP); Hitoshi Harigae, Tokyo (JP); Masayuki Kataoka, Tokyo (JP)

(73) Assignees: Shiseido Co., Ltd., Tokyo (JP); Soda Aromatic Co., Ltd., Tokyo (JP)

( * ) Notice: Subject to any disclaimer, the term of this patent is extended or adjusted under 35 U.S.C. 154(b) by 506 days.

(21) Appl. No.: 09/857,618

(22) PCT Filed: May 31, 2000

(86) PCT No.: PCT/JP00/03522

§ 371 (c)(1),
(2), (4) Date: Jun. 7, 2001

(87) PCT Pub. No.: WO00/78117

PCT Pub. Date: Dec. 28, 2000

(51) Int. Cl.
*A61K 7/46* (2006.01)

(52) U.S. Cl. .............................. 512/1; 512/5; 424/401

(58) Field of Classification Search .................... 512/1, 512/5; 424/401
See application file for complete search history.

(56) References Cited

U.S. PATENT DOCUMENTS

| | | | | |
|---|---|---|---|---|
| 4,444,982 A * | 4/1984 | Nagashima et al. | ........ | 568/817 |
| 4,847,422 A * | 7/1989 | Klemola et al. | ............ | 568/438 |
| 4,920,096 A * | 4/1990 | Bedoukian | ..................... | 512/5 |
| 5,321,006 A * | 6/1994 | Mookherjee et al. | .......... | 512/5 |
| 5,895,657 A * | 4/1999 | Fournet et al. | ............. | 424/401 |

FOREIGN PATENT DOCUMENTS

DE 195 32 017 3/1997

OTHER PUBLICATIONS

Japanese Patent Office, Patent Abstracts of Japan, Publication No.: 06-093287, Date of Publication: Apr. 5, 1994, Application No.: 04-284879, Date of Filing: Sep. 11, 1992 (See document XP002156947—in IDS filed with USPTO Jun. 7, 2001).

Japanese Patent Application 06-93287, Published Apr. 5, 1994, Database WPI, Derwent Publications Ltd., London, GB, XP002156947.

* cited by examiner

*Primary Examiner*—Monique T. Cole
(74) *Attorney, Agent, or Firm*—Snider & Associates; Ronald R. Snider

(57) ABSTRACT

A method of collection of the fragrance ingredient of fragrant wood comprises extracting an essential oil ingredient by a solvent from the fragrant wood and collecting the fragrance ingredient in a vapor-phase by heating the extract, a perfume composition contains the fragrance ingredient, and a cosmetic contains the fragrance ingredient. The fragrance ingredient is obtained without a burnt smell, and it has an aroma of the fragrant wood.

11 Claims, 1 Drawing Sheet

METHOD OF COLLECTION OF FRAGRANCE INGREDIENT, PERFUME COMPOSITION CONTAINING THIS FRAGRANCE INGREDIENT AND COSMETICS CONTAINING THIS FRAGRANCE INGREDIENT

TECHNICAL FIELD

The present invention relates to an improved method of collection a fragrance ingredient and a perfume composition containing the fragrance ingredient and a cosmetic containing the fragrance ingredient. The invention provides an improvement of the fragrance quality of a perfume composition containing the fragrance ingredient. Also, the invention provides an improvement of the fragrance quality of a cosmetic containing the fragrance ingredient.

BACKGROUND ART

An agarwood is the fragrant wood containing the resin that has unique aroma. The producing district of agarwood is found mainly in Southeast Asia. The fragrance of the agarwood obtained by heating or burning was used as incense. Especially among the agarwood, the high quality agarwood called "Kyara", is highly prized.

Conventionally, the collection method of fragrance ingredient from a fragrant wood is by the thermal decomposition of the fragrant wood powder with a mixed gas as described in Japanese Unexamined Patent Publication No. Hei 6-93287. However, this collection method had a disadvantage that a burnt smell depending on the dry distillation of fragrant wood can not be removed. Also, this method is a complicated method that requires a special apparatus and an adjustment of heating temperature and mixed gas. Also, the decomposition product of fragrant wood yields ingredient other than original fragrance ingredient and the colored solution. Therefore, it was impossible to reproduce the original aroma of agarwood completely from the collected fragrance ingredient of the prior art.

DISCLOSURE OF INVENTION

An object of the present invention is to provide a method that collects only desirable fragrance ingredient effectively without a burnt smell. It is an object to reproduce the original aroma of fragrant wood from fragrant wood. It is further object of the present invention is to provide an application of the original aroma fragrance ingredient to the various fragrance products and cosmetics.

As a result of diligent study by the present inventors, the present invention has been accomplished. The present inventors have found that use of solvent extraction is able to achieve the above objects.

A method of collection of a fragrance ingredient of the present invention comprises extracting the essential oil ingredient by solvent from a fragrant wood and collecting the fragrance ingredient in vapor-phase by heating the extract.

Also, in the method of collection of the fragrance ingredient of the present invention, it is preferable that said fragrance ingredient is discharged forcibly from a heating container by introducing an inert gas.

Also, in the method of collection of the fragrance ingredient of the present invention, it is preferable that said fragrance ingredient is collected to an absorption solvent and get a resultant as a fragrance collection liquid.

Also, in the method of collection of the fragrance ingredient of the present invention, it is preferable that said fragrant wood is agarwood.

Also, a perfume composition of the present invention contains said fragrance ingredient by means of the method of collection of the fragrance ingredient.

Also, in the perfume composition of the present invention, it is preferable that said perfume composition contains a fragrant wood extract.

Also, in the perfume composition of the present invention, it is preferable that a ratio of the fragrance collection solution/said fragrant wood extract is 0.25 to 9.

Also, in the perfume composition of the present invention, it is preferable that said perfume composition has an aroma of agarwood.

Also, a cosmetic of the present invention contains said fragrance ingredient by means of the method of collection of the fragrance ingredient.

Also, in the cosmetic of the present invention, it is preferable that said cosmetic contains a fragrant wood extract.

Also, in the cosmetic of the present invention, it is preferable that a ratio of the fragrance collection liquid/said fragrant wood extract is 0.25 to 9.

BEST MODE FOR CARRYING OUT THE INVENTION

Figure 1:
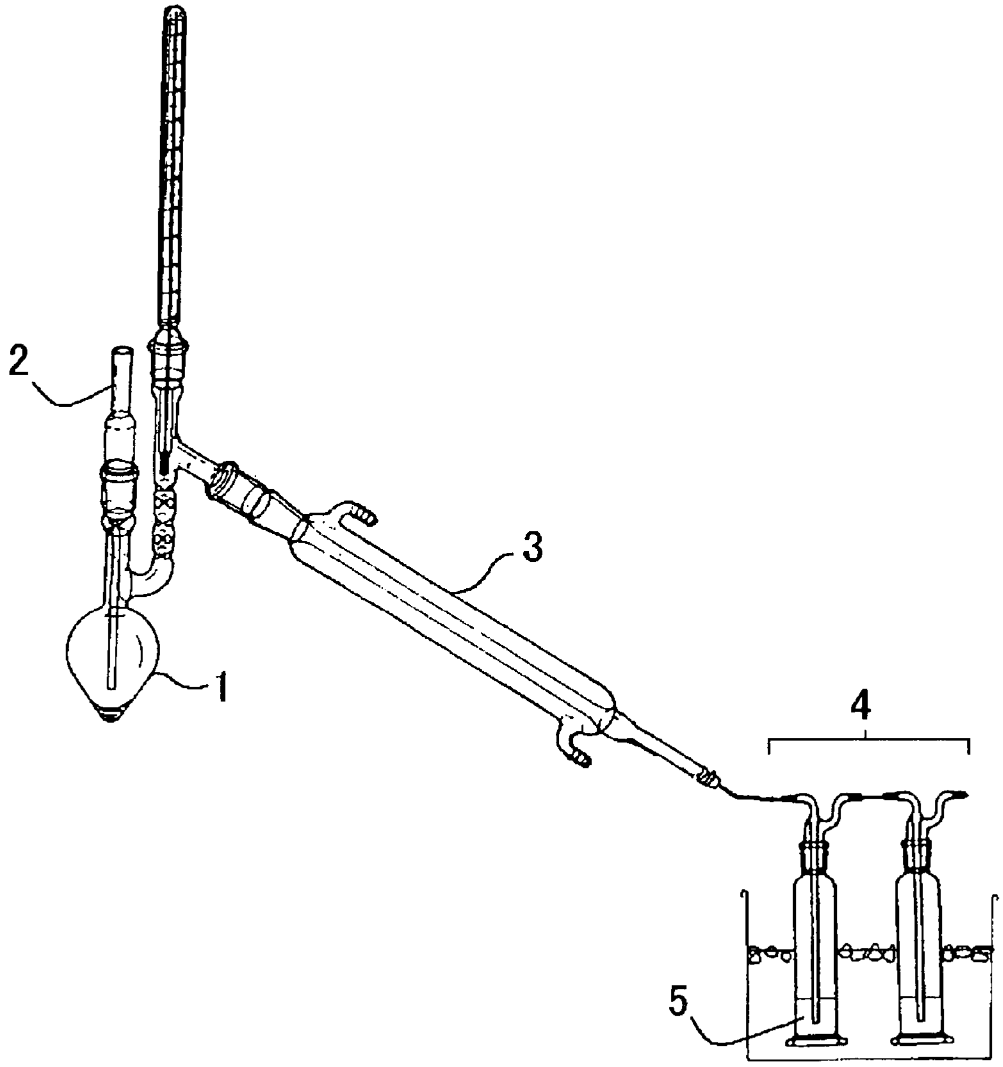
FIG. 1 shows one example of the fragrance collection apparatus that is used for the present invention.

The following is the explanation of the details for the collection method of a fragrance ingredient of the present invention.

Powder or chips of fragrant wood is processed by heating agitation extraction or by soaking extraction for extracting the essential oil ingredient. After filtering, the extract is obtained by removing the solvent. This extract is heated and the volatized fragrance in the head space is led outside the system. The introduction of inert gas is more suitable. The fragrance ingredient is collected in an absorption solvent which becomes a fragrance collection liquid. By this method, a fragrance ingredient that reproduces the original fragrance of fragrant wood is obtained. Also, the perfume composition containing this fragrance collection liquid can reproduce the original fragrance of the fragrant wood. Also, the cosmetic containing this fragrance collection liquid can improve the quality of aroma.

Extraction of Fragrance Ingredient

In the present invention, the powder or the pieces of the fragrant wood can be used suitably as a fragrant wood material. The fragrant wood in the present invention is a agarwood or a sandalwood etc. The agarwood is grouped into 6 kinds which is called "Rikkoku".

"Rikkoku" is derived from producing district of the fragrant wood, i.e. "Kyara", "Rakoku", "Manaban", "Manaka", "Sasora", "Sumotara" etc. Many of the fragrant woods are produced from the hinterland of Vietnam, Cambodia and Myanmar. However, the differentiation of a producing district becomes meaningless now. The quality of tree is decided on the basis of the figure and aroma of fragrant wood.

A solvent is used to extract the essential oil ingredient containing the fragrance ingredient in the fragrant wood in the present invention. Water, methanol, ethanol, isopropanol, diethylether, pentane, hexane, propyleneglycol, glycerin etc. or these mixture solvent etc. are used for the solvent that extracts the essential oil ingredient containing the fragrance ingredient of the fragrant wood.

In the present invention, addition of the solvent for the extraction of 10 to 100 weight times to fragrant wood is desirable. Addition of the solvent for the extraction of 20 to 70 weight times to fragrant wood is more desirable. By this solvent extraction, the essential oil ingredient containing fragrance ingredient is extracted. As for extraction method, by the method of the public knowledge such as the heating extraction with agitation or the soaking extraction processing by using the solvent, the essential oil ingredient containing fragrance ingredient can be extracted.

A desirable process that extracts the essential oil ingredient which contains ingredients from fragrant wood is, for example, the extraction processing in 3 to 6 hours at 40° C. to 60° C. using heating extraction with agitation. Also, for example, it is desirable to extract for 1 to 10 days at room temperature using soaking extraction. Next, the crude extract (the essential oil ingredient) that is obtained is treated with solid-liquid separation by the optional method such as filtration or centrifugation. Furthermore the separated liquid that is obtained is concentrated and the extract is obtained. As for the concentration method of the separated liquid, for example, the method of public knowledge can be used, such as distilling and removing solvent under reduced pressure by the rotary evaporator.

Collection of Fragrance Ingredient

Next, the concentration extract that is obtained by the above described process is inserted into the fragrance collection apparatus. The fragrance ingredient volatilized by heating is discharge forcibly through collection apparatus by the aeration of an inert gas, and is collected to the absorption solvent inside the collection apparatus.

FIG. 1 shows one example of the fragrance collection apparatus that is used to the collection method of the fragrance ingredient of the present invention. In FIG. 1, the concentrated extraction liquid is heated in the heating container 1 together with an inert gas introduced through introduction pipe 2. The fragrance ingredient volatilizes in heating container 1. Next, the fragrance ingredient with the inert gas that is introduced from introduction pipe 2 which passes through the connection pipe 3, is introduced to the collection apparatus 4, and is collected in absorption solvent 5. In the present invention, an agitation apparatus can be attached to the heating container 1. Also, by using a drum style container or a flask style container as the heating container, it can also be heated with rotation. The collection apparatus can use either countercurrent contact style or batch style. In the case of batch style, it is desirable to connect 2 to 3 collection apparatuses to improve collection efficiency. Also it is desirable to cool the absorption solvent with ice water etc. to improve collection efficiency. Also, to increase gas-liquid interface, it is possible to make the tip part of the introduction pipe perforated pipe style. Also it is possible to destroy or make small bubles physically by agitation apparatus etc.

The heating temperature of the above-mentioned heating container 1 is preferably in the ranges of 150° C. to 200° C. Nitrogen, argon and carbon dioxide etc. gas used for inert gas. A gas flow rate for 1 g of extract oil is preferably the range of 20 ml/min to 200 ml/min. Also, according to the type of use of the collection liquid, methanol, ethanol, isopropanol, diethyl ether, pentane, hexane, hydrated methanol, hydrated ethanol, propylene glycol, dipropylene glycol etc. are used as absorption solvent. The amount of absorption solvent is preferably 10 to 100 times the amount of said extract. Also, preferably the absorption solvent is cooled. The preferable cooling temperature is 0 to 10° C.

Perfume Composition

The fragrance ingredient that was collected in this way is preserved as the fragrance collection liquid which contains the fragrance ingredient. A perfume composition can contain the fragrance collection liquid combined with another perfume in optional proportion. By adding an extract of the fragrant wood to the perfume composition of the present invention, an improved more excellent aroma of fragrant wood can be reproduced. The manufacturing method of extract of the fragrant wood is sufficient with the method of public knowledge. A ratio by weight of fragrance collection liquid/fragrant wood extract is preferably approximately 0.25 to 9. In the case that this ratio missed, the original fragrance of fragrant wood may be damaged.

Also, the perfume composition in the present invention includes any product that is the perfume fragrance with except for food mainly, for example perfume, colon, bath agents, various kinds cleaners, sanitation articles, incense sticks, aromatics etc.

Cosmetics

The fragrance ingredient of the present invention can be added to the cosmetics and the like. The cosmetics of the present invention are, for example perfume, colon, foundation, lotion, cosmetic cream, cosmetic gel, hair dressing etc.; toiletry products such as soap, detergent, shampoo, rinse etc. The cosmetics of the present invention are the product that can contain fragrance in the perfume other than food mainly.

By adding an extract of the fragrant wood to the perfume composition of the present invention, an improved more excellent aroma of fragrant wood can be obtained. The manufacturing method of extract of the fragrant wood is sufficient with the method of public knowledge. A ratio by weight of fragrance collection liquid/fragrant wood extract is preferably approximately 0.25 to 9. In the case that this ratio missed, the original fragrance of fragrant wood may be damaged.

The following is the detailed explanation of the present invention by working examples.

Collection Method of Fragrance Ingredient

WORKING EXAMPLE 1

10 g of powder of fragrant wood "Kyara" was placed into 500 ml of Erlenmeyer flask with a plug and was extracted with 300 g of diethyl ether for 10 days at room temperature. Then, the wood powder was separated from extract liquid by filtration. Diethyl ether was removed by evaporator under reduced pressure.

Next, the extract oil was transferred to Claisen flask type distillation apparatus, was heated to 180° C. with an oil bath. Nitrogen gas was introduced with flow rate of 300 ml/min. The fragrance ingredient was collected for 60 minutes. In the collection method, 30 ml of 95% ethanol was used as absorption solvent. The distilled fragrance ingredient with the gas was collected in the absorption solvent by a introducing tube whose exit was in the absorption solvent. The collection apparatus was connected in series (30 ml×2) and the fragrance ingredient volatilized was collected. Considering increasing collection efficiency, the absorption solvent was cooled with an ice water bath.

WORKING EXAMPLE 2

The solvent that extracts fragrant wood was changed into methanol, and the extraction processing of the method similar to Working example 1 was carried out. Next, in the condition similar to Working example 1, the extract oil was transferred to Claisen flask type distillation apparatus, was heated to 180° C. with an oil bath. Nitrogen gas was introduced with flow rate of 300 ml/min. The fragrance ingredient was collected for 60 minutes. In the collection method, 30 ml of 95% ethanol was used as absorption solvent. The distilled fragrance ingredient with the gas was collected in the absorption solvent by a introducing tube whose exit was in the absorption solvent. The collection apparatus was connected in series (30 ml×2) and the fragrance ingredient volatilized was collected. Considering increasing collection efficiency, the absorption solvent was cooled with an ice water bath.

WORKING EXAMPLE 3

The solvent that extracts fragrant wood was changed into 95% ethanol, and the extraction processing of the condition similar to Working example 1 was carried out and the extract was obtained by removing the solvent. Next, by the condition similar to Working example 1, the extract oil was transferred to Claisen flask type distillation apparatus, was heated to 180° C. with an oil bath. Nitrogen gas was introduced with flow rate of 300 m/min. The fragrance ingredient was collected for 60 minutes. In the collection method, 30 ml of 95% ethanol was used as absorption solvent. The distilled fragrance ingredient with the gas was collected in the absorption solvent by a introducing tube whose exit was in the absorption solvent. The collection apparatus was connected in series (30 ml×2) and the fragrance ingredient volatilized was collected. Considering increasing collection efficiency, the absorption solvent was cooled with an ice water bath.

WORKING EXAMPLE 4

The solvent that extracts fragrant wood was changed into hexane, and the extraction processing of the condition similar to Working example 1 was carried out and the extract was obtained by removing the solvent. Next, by the condition similar to Working example 1, the extract oil was transferred to Claisen flask type distillation apparatus, was heated to 180° C. with an oil bath. Nitrogen gas was introduced with flow rate of 300 ml/min. The fragrance ingredient was collected for 60 minutes. In the collection method, 30 ml of 95% ethanol was used as absorption solvent. The distilled fragrance ingredient with the gas was collected in the absorption solvent by a introducing tube whose exit was in the absorption solvent. The collection apparatus was connected in series (30 ml×2) and the fragrance ingredient volatilized was collected. Considering increasing collection efficiency, the absorption solvent was cooled with an ice water bath.

WORKING EXAMPLE 5

By the method similar to Working example 1, the extraction processing of fragrant wood was carried out with diethyl ether and the extract was obtained by removing the solvent. Next, by the condition similar to Working example 1, the extract oil was transferred to Claisen flask type distillation apparatus, was heated to 150° C. with an oil bath. Nitrogen gas was introduced with flow rate of 300 ml/min. The fragrance ingredient was collected for 60 minutes. In the collection method, 30 ml of 95% ethanol was used as absorption solvent. The distilled fragrance ingredient with the gas was collected in the absorption solvent by a introducing tube whose exit was in the absorption solvent. The collection apparatus was connected in series (30 ml×2) and the fragrance ingredient volatilized was collected. Considering increasing collection efficiency, the absorption solvent was cooled with an ice water bath.

WORKING EXAMPLE 6

By the method similar to Working example 1, the extraction processing of fragrant wood was carried out with diethyl ether and the extract was obtained by removing the solvent. Next, by the condition similar to Working example 1, the extract oil was transferred to Claisen flask type distillation apparatus, was heated to 200° C. with an oil bath. Nitrogen gas was introduced with flow rate of 300 ml/min. The fragrance ingredient was collected for 60 minutes. In the collection method, 30 ml of 95% ethanol was used as absorption solvent. The distilled fragrance ingredient with the gas was collected in the absorption solvent by a introducing tube whose exit was in the absorption solvent. The collection apparatus was connected in series (30 ml×2) and the fragrance ingredient volatilized was collected. Considering increasing collection efficiency, the absorption solvent was cooled with an ice water bath.

COMPARATIVE EXAMPLE 1

An dry distillated collection liquid was obtained from the fragrant wood powder by dry distillation with the apparatus similar to Working example 1. Next, the extract oil was transferred to Claisen flask type distillation apparatus, and it was heated to 180° C. with an oil bath. Nitrogen gas was introduced with flow rate of 300 ml/min. The fragrance ingredient was collected for 60 minutes. In the collection method, 30 ml of 95% ethanol was used as absorption solvent. The distilled fragrance ingredient with the gas was collected in the absorption solvent by an introducing tube whose exit was in the absorption solvent. The collection apparatus was connected in series (30 ml×2) and the fragrance ingredient volatilized was collected. Considering increasing collection efficiency, the absorption solvent was cooled with an ice water bath. The dry distillation collection liquid that was collected was compared with Working example 1 of the present invention method.

Table 1 and Table 2 show the result of the extraction process with regard to Working examples 1 to 6 and Comparative example 1.

TABLE 1

| | Extraction condition | | | |
|---|---|---|---|---|
| | Extraction solvent | | Fragrant wood | Extraction |
| | Kind | Amount | Amount | time |
| Comp. Ex. 1 | — | — | 10 g | — |
| Work. Ex. 1 | Diethyl ether | 300 g | 10 g | 7 days |
| Work. Ex. 2 | Methanol | 300 g | 10 g | 7 days |
| Work. Ex. 3 | 95% Ethanol | 300 g | 10 g | 7 days |
| Work. Ex. 4 | Hexane | 300 g | 10 g | 7 days |
| Work. Ex. 5 | Diethyl ether | 300 g | 10 g | 7 days |
| Work. Ex. 6 | Diethyl ether | 300 g | 10 g | 7 days |

TABLE 2

| | Extraction result | |
|---|---|---|
| | Extract amount | Coloring |
| Comp. Ex. 1 | — | — |
| Work. Ex. 1 | 2.67 g | Liver brown |
| Work. Ex. 2 | 2.44 g | Light-brown |
| Work. Ex. 3 | 2.51 g | Light-brown |
| Work. Ex. 4 | 2.78 g | Dark brown |
| Work. Ex. 5 | 2.58 g | Liver brown |
| Work. Ex. 6 | 2.60 g | Liver brown |

Table 3 shows the parameters of the methods of the heating fragrance collection process with regard to Working examples 1 to 6 and Comparative example 1.

TABLE 3

| | Fragrance ingredient collection condition | | | | | |
|---|---|---|---|---|---|---|
| | | Flow | | Collection Solvent | | Collection |
| | Gas | Rate | Temp. | Kind | Amount | Time |
| Comp. Ex. 1 | Nitrogen | 300 ml | 180° C. | 95% Ethanol | 100 g | 60 min |
| Work. Ex. 1 | Nitrogen | 300 ml | 180° C. | 95% Ethanol | 100 g | 60 min |
| Work. Ex. 2 | Nitrogen | 300 ml | 180° C. | 95% Ethanol | 100 g | 60 min |
| Work. Ex. 3 | Nitrogen | 300 ml | 180° C. | 95% Ethanol | 100 g | 60 min |
| Work. Ex. 4 | Nitrogen | 300 ml | 180° C. | 95% Ethanol | 100 g | 60 min |
| Work. Ex. 5 | Nitrogen | 300 ml | 150° C. | 95% Ethanol | 100 g | 60 min |
| Work. Ex. 6 | Nitrogen | 300 ml | 200° C. | 95% Ethanol | 100 g | 60 min |

Table 4 shows the evaluation of aroma with regard to Working examples 1 to 6 and Comparative example 1.

TABLE 4

| | Evaluation of fragrance collection liquid | | |
|---|---|---|---|
| | Coloring | Aroma | Burnt smell |
| Comp. Ex. 1 | Colorless | Woody aroma with burnt smell | Yes |
| Work. Ex. 1 | Colorless | Woody aroma with density | No |
| Work. Ex. 2 | Colorless | Woody aroma with mellowness | No |
| Work. Ex. 3 | Colorless | Woody aroma with mellowness | No |
| Work. Ex. 4 | Colorless | Woody aroma with slight quietude | No |
| Work. Ex. 5 | Colorless | Woody aroma with density | No |
| Work. Ex. 6 | Colorless | Sweet aroma with animal smell | No |

*The total of absorption liquid in two trap was evaluated regarding aroma.

In Table 4, it is understood that the collection liquid of Comparative example 1 by dry distillation without extraction has a big fault that there is a burnt smell which is not desired as perfume material, although there is also woody aroma. As the result of Working examples 1 to 6, it is shown that no burnt smell exists at all, although there is a different aroma depending on kind of the extract solvent. Also, because the burnt smell is not collected from the head space from the heating to 250° C., most of the extracted ingredients are presumed to be oily ingredients. The extracted oil showed fairly deep brown to light-brown color in the extracts of any solvent (see Table 2). However, the fragrance collection liquid of the present invention was estimated to be colorless (see Table 4), which means that the part of the aroma is only collected.

Perfume Composition

As the example of the perfume composition containing the fragrance collection liquid that was obtained from fragrant wood, the perfume composition for incense stick is shown in Table 5. Also, the result of the evaluation of the smell quality in the sensing test is shown in Table 5, which was evaluated. The evaluation standard is as follows. The evaluated values are average of 20 panels of specialist.

(Evaluation Standard)

3: The smell quality with the aroma of fragrant wood was excellent

2: The smell quality with the aroma of fragrant wood was excellent slightly

1: The smell quality with the aroma of fragrant wood was inferior slightly

0: The smell quality with the aroma of fragrant wood was inferior considerably

TABLE 5

| No. | Perfume material | Comp. Ex. 2 | Work. Ex. 7 | Comp Ex. 3 |
|---|---|---|---|---|
| 1 | Benzyl cinnamate | 13 | 13 | 13 |
| 2 | Raspberry Ketone | 4 | 4 | 4 |
| 3 | Vanillin | 7 | 7 | 7 |
| 4 | Ethyl vanillin | 3 | 3 | 3 |
| 5 | Coumarin | 40 | 40 | 40 |
| 6 | Vetiveryl acetate | 3 | 3 | 3 |
| 7 | Sandalwood oil | 60 | 60 | 60 |
| 8 | Ambroxan | 3 | 3 | 3 |
| 9 | Ethyl cinnamate | 15 | 15 | 15 |
| 10 | Methyl cinnamate | 10 | 10 | 10 |
| 11 | Cinnamic aldehyde | 10 | 10 | 10 |
| 12 | Phenylethyl alcohol | 250 | 250 | 250 |
| 13 | Benzyl alcohol | 45 | 45 | 45 |
| 14 | Benzaldehyde | 7 | 7 | 7 |
| 15 | Bergamotal | 20 | 20 | 20 |
| 16 | Fragrance collection liquid | — | 10 | — |
| 17 | Dry distillation collection liquid | — | — | 10 |
| | Total (by weight) | 490 | 500 | 500 |
| | Evaluation | — | 3 | 0 |

In Table 5, it is understood that the perfume composition of Working example 7 containing the fragrant wood fragrance collection liquid obtained by the method of the present invention from fragrant wood has excellent agarwood aroma. On the other hand, Comparative example 3 containing dry distillation collection liquid had nasty and burnt smell, which degraded the smell quality. Also, in the comparison of between the aroma of Working example 7 and Comparative example 3, a higher-class impression was recognized in Working example 7 than Comparative example 3. The aroma of Working example 7 had a deep woody aroma which derives more natural feeling.

Next, as the example of the perfume composition containing the fragrance collection liquid that was obtained from fragrant wood, the perfume composition for the cosmetics is shown in Table 6. The present inventors tried to add the fragrant wood extract for reproducing better agarwood fragrance. The evaluation standard is as follows. The evaluated values are the average of 20 panels of specialist.

(Evaluation Standard)

±: Working example 8 (Comparison standard)

+: The smell quality with fragrant wood was improved in comparison with Working example 8

−: The smell quality with fragrant wood was inferior in comparison with Working example 8

The result is shown in Table 6.

TABLE 6

| | Perfume material | Work. Ex. 8 | Work Ex. 9 | Comp. Ex. 4 |
|---|---|---|---|---|
| 1 | Cedarwood oil | 150 | 150 | 150 |
| 2 | Iso E super(*1) | 150 | 150 | 150 |
| 3 | Phenylethyl alcohol | 100 | 100 | 100 |
| 4 | Hedion(*2) | 100 | 100 | 100 |
| 5 | Sandalore(*3) | 80 | 80 | 80 |
| 6 | Galaxolide(*4) | 80 | 80 | 80 |
| 7 | Bergamot oil | 70 | 70 | 70 |
| 8 | α-Isomethyl ionone | 50 | 50 | 50 |
| 9 | Lilial(*5) | 50 | 50 | 50 |
| 10 | Lyral(*6) | 30 | 30 | 30 |
| 11 | Eugenol | 30 | 30 | 30 |
| 12 | Muscone | 30 | 30 | 30 |
| 13 | Cypress oil | 20 | 20 | 20 |
| 14 | Patchouli oil | 20 | 20 | 20 |
| 15 | Vanillin | 10 | 10 | 10 |
| 16 | Rose oil | 5 | 5 | 5 |
| 17 | Clove oil | 5 | 5 | 5 |
| 18 | Oakmoss absolute | 5 | 5 | 5 |
| 19 | Cinnamon bark oil | 3 | 3 | 3 |
| 20 | Ylang ylang oil | 2 | 2 | 2 |
| 21 | Fragrance collection liquid | 10 | 5 | — |
| 22 | Fragrant wood extract | — | 5 | 10 |
| | Total (by weight) | 1000 | 1000 | 1000 |
| | Smell quality evaluation | ± | + | − |

*1 Trade name of IFF Inc.
*2 Trade name of Firmenich Inc.
*3 Trade name of Givaudan-Roure Inc.
*4 Trade name of IFF Inc.
*5 Trade name of Givaudan-Roure Inc.
*6 Trade name of IFF Inc.

(Manufacturing Method of Fragrant Wood Extract)

Chips of agarwood ("Kyara") was kept to stand for 10 days in ethanol solution of 19 weight times the agarwood. After filtering, decoloring process was carried out with active carbon. The decolored solution was filtered and a crude extract of the agarwood was obtained. Under the reduced pressure the ethanol is removed by an evaporator and the fragrant wood extract was obtained.

In Table 6, it is shown that smell quality was improved by adding fragrance collection liquid and fragrant wood extract. Also, it is shown that excellent aroma is not obtained in the composition containing the fragrant wood extract only.

Next, the weight ratio of fragrance collection liquid to fragrant wood extract was studied by using composition of Table 5. The evaluation standard is as follows. The evaluated values are the average of 20 panels of specialist.

(Evaluation Standard)

2: The smell quality was improved in comparison with Working example 8

1: The smell quality was improved slightly in comparison with Working example 8

0: The smell quality did not change in comparison with Working example 8 or the smell quality was inferior to Working example 8

The result is shown in Table 7.

TABLE 7

| | Test example | | | | | | |
|---|---|---|---|---|---|---|---|
| Perfume material | 1 | 2 | 3 | 4 | 5 | 6 | 7 |
| Cedarwood oil | 150 | 150 | 150 | 150 | 150 | 150 | 150 |
| Iso E soper (*1) | 150 | 150 | 150 | 150 | 150 | 150 | 150 |
| Phenylethyl alcohol | 100 | 100 | 100 | 100 | 100 | 100 | 100 |
| Hedion (*2) | 100 | 100 | 100 | 100 | 100 | 100 | 100 |
| Sandalore (*3) | 80 | 80 | 80 | 80 | 80 | 80 | 80 |
| Galaxolide (*4) | 80 | 80 | 80 | 80 | 80 | 80 | 80 |
| Bergamot oil | 70 | 70 | 70 | 70 | 70 | 70 | 70 |
| α-Isomethyl ionone | 50 | 50 | 50 | 50 | 50 | 50 | 50 |
| Lilial (*5) | 50 | 50 | 50 | 50 | 50 | 50 | 50 |
| Lyral (*6) | 30 | 30 | 30 | 30 | 30 | 30 | 30 |
| Eugenol | 30 | 30 | 30 | 30 | 30 | 30 | 30 |
| Muscone | 30 | 30 | 30 | 30 | 30 | 30 | 30 |
| Cypress oil | 20 | 20 | 20 | 20 | 20 | 20 | 20 |
| Patchouli oil | 20 | 20 | 20 | 20 | 20 | 20 | 20 |
| Vanillin | 10 | 10 | 10 | 10 | 10 | 10 | 10 |
| Rose oil | 5 | 5 | 5 | 5 | 5 | 5 | 5 |
| Clove oil | 5 | 5 | 5 | 5 | 5 | 5 | 5 |
| Oakmoss absolute | 5 | 5 | 5 | 5 | 5 | 5 | 5 |
| Cinnamon bark oil | 3 | 3 | 3 | 3 | 3 | 3 | 3 |
| Ylang ylang oil | 2 | 2 | 2 | 2 | 2 | 2 | 2 |
| Fragrance collection liquid | 1 | 2 | 3 | 5 | 8 | 9 | 0 |
| Fragrant wood extract | 9 | 8 | 7 | 5 | 2 | 1 | 10 |
| Total (by weight) | 1000 | 1000 | 1000 | 1000 | 1000 | 1000 | 1000 |
| Ratio (*) | 0.11 | 0.25 | 0.43 | 1.00 | 4.00 | 9.00 | 0.00 |
| Evaluation | 0 | 1 | 2 | 2 | 2 | 1 | 0 |

(*1) Trade name of IFF Inc.
(*2) Trade name of Firmenich Inc.
(*3) Trade name of Givaudan-Roure Inc.
(*4) Trade name of IFF Inc.
(*5) Trade name of Givaudan-Roure Inc.
(*6) Trade name of IFF Inc.
(*) Ratio = Fragrance collection liquid/Fragrant wood extract In Table 5, it is understood that the ratio of the fragrance collection liquid/the fragrant wood extract is preferably 0.25 to 9.

The working example of perfume composition for the perfume is shown in Table 8.

TABLE 8

| Perfume material | Working example 10 |
|---|---|
| Phenylethyl alcohol | 200 |
| α-Isomethyl ionone | 150 |
| Iso E super(*1) | 150 |
| Hedion(*2) | 100 |
| Lilial(*3) | 100 |
| Lyral(*4) | 80 |
| Hexyl cinnamic aldehyde | 50 |
| Geraniol | 30 |
| Eugenol | 30 |
| Habanolide(*5) | 30 |
| Bergamot oil | 20 |
| Processed-valerian | 20 |
| Muscone | 10 |
| Jasmine oil | 5 |
| Vanillin | 5 |
| Rose oil | 3 |
| Tonka beans absolute | 3 |
| Benzoin Resinoid | 3 |
| Oakmoss absolute | 3 |
| Helional(*6) | 2 |
| Patchouli oil | 2 |
| Ambrette seed oil | 1 |
| Orris concrete | 1 |
| Fragrance collection liquid | 1 |
| Tatal (by weight) | 1000 |

*1 Trade name of IFF Inc.
*2 Trade name of Firmenich Inc.
*3 Trade name of Givaudan-Roure Inc.
*4 Trade name of IFF Inc.
*5 Trade name of Firmenich Inc.
*6 Trade name of IFF Inc.

As explained with the working examples of the present invention, a method of collection of fragrance ingredient of the present invention comprises solvent extraction of an essential oil ingredient from a fragrant wood and collection of the fragrance ingredient in vapor-phase obtained by heating the extract. Accordingly, because the fragrance ingredient obtained has not burnt smell at all, it can be utilized as material for various uses. Only the fragrance part of the fragrant wood can be utilized fully. Namely, without being limited to conventional incense, incense stick etc., the application and the utilization of the wide area of perfume, cosmetics, aromatic etc. becomes possible.

Also, by adding the fragrant wood extract to the fragrance ingredient of the present invention, an aroma quality can be improved. The fragrance of fragrant wood can be reproduce more accurately.

What is claimed is:

1. A method of collection of a fragrance ingredient which comprises the steps of:

(a) extracting an essential oil ingredient containing the fragrance ingredient by solvent from a fragrant wood;

(b) filtering the fragrant wood from the extract and solvent;

(c) obtaining the extract by removing the solvent;

(d) volatizing the fragrance ingredient into vapor-phase by heating the extract, and introducing an inert gas into forcibly discharge the fragrance ingredient from a heating container; and (e) collecting the fragrance ingredient in an absorption solvent to obtain a fragrance collection liquid.

2. The method of collection of the fragrance ingredient according to claim 1, wherein the fragrant wood is agarwood.

3. A perfume composition comprising the fragrance collection liquid which collects the fragrance ingredient by means of the method of collection of the fragrance ingredient according to claim 1.

4. The perfume composition according to claim 3, wherein the perfume composition contains a fragrant wood extract.

5. The perfume composition according to claim 4, wherein a ratio by weight of the fragrance collection liquid and the fragrant wood extract (fragrance collection liquid/fragrance wood extract) is 0.25 to 9.

6. The perfume composition according to claim 3, wherein said perfume composition has an aroma of agarwood.

7. A cosmetic comprising the fragrance collection liquid which collects the fragrance ingredient by means of the method of collection of the fragrance ingredient according to claim 1.

8. The cosmetic according to claim 7, wherein said cosmetic contains a fragrant wood extract.

9. The cosmetic according to claim 8, wherein a ratio by weight of the fragrance collection liquid and the fragrant wood extract (fragrance collection liquid/fragrance wood extract) is 0.25 to 9.

10. A perfume composition comprising a fragrance collection liquid which collects a fragrance ingredient by means of the method according to claim 1 wherein the perfume composition contains a fragrant wood extract, and wherein a ratio by weight of the fragrance collection liquid and the fragrant wood extract (fragrance collection liquid/fragrance wood extract) is 0.25 to 9.

11. A cosmetic comprising a fragrance collection liquid which collects a fragrance ingredient by means of the method according to claim 1 wherein said cosmetic contains a fragrant wood extract, and wherein a ratio by weight of the fragrance collection liquid and the fragrant wood extract (fragrance collection liquid/fragrance wood extract) is 0.25 to 9.

* * * * *